United States Patent [19]

Monaco et al.

[11] Patent Number: 5,771,499
[45] Date of Patent: Jun. 30, 1998

[54] SAFETY GOGGLES HAVING FOAMED-IN-PLACE FACE GASKET

[75] Inventors: Michael Angelo Monaco, North Tonawanda; Daniel Wayne Morley, East Bloomfield, both of N.Y.

[73] Assignees: American Allsafe Company, Tonawanda; TMP Technologies, Inc., Buffalo, both of N.Y.

[21] Appl. No.: 648,498

[22] Filed: May 15, 1996

[51] Int. Cl.$^6$ ........................................................ A61F 9/02
[52] U.S. Cl. ...................................... 2/428; 2/431; 2/437
[58] Field of Search ......................... 2/440, 428, 430, 2/431, 439, 436, 437

[56] References Cited

U.S. PATENT DOCUMENTS

| | | | |
|---|---|---|---|
| 1,306,357 | 6/1919 | Shindel | 2/439 |
| 2,406,608 | 8/1946 | Joyce | 2/440 |
| 2,918,676 | 12/1959 | Matheson | 2/440 |
| 3,638,240 | 2/1972 | Militello | 2/437 |
| 3,725,953 | 4/1973 | Johnson et al. | 2/428 |
| 4,069,516 | 1/1978 | Watkins, Jr. | 2/428 |
| 4,087,865 | 5/1978 | Garofalo | 2/428 |
| 4,665,570 | 5/1987 | Davis | 2/428 |
| 4,689,837 | 9/1987 | Bolle | 2/440 |
| 4,755,040 | 7/1988 | Haslbeck | 351/43 |
| 4,796,308 | 1/1989 | Bourgeois | 2/243 |
| 4,896,380 | 1/1990 | Kamatani | 2/428 |
| 5,216,759 | 6/1993 | Hewitt et al. | 2/439 |
| 5,339,119 | 8/1994 | Gardner | 351/158 |

*Primary Examiner*—Peter Nerbun
*Attorney, Agent, or Firm*—Dennis T. Griggs

[57] ABSTRACT

A face gasket made of a smooth, non-tacky, low durometer, chemically resistant closed cell resin foam is attached onto a goggles frame by injecting the resin into a mold cavity containing a contoured rim portion of the goggles frame. The contoured rim portion is intersected by multiple sprue openings that permit the pressurized resin to flow through the goggles frame and around the contoured rim during molding. The contoured rim portion is embedded within the molded gasket and sprue slugs extend through and fill the openings. The sprue slugs are integrally formed with the main body of the face gasket, thereby defining attachment links that permanently connect the face gasket in splash sealing engagement around the contoured rim and along internal and external sidewall surfaces of the goggles frame.

10 Claims, 3 Drawing Sheets

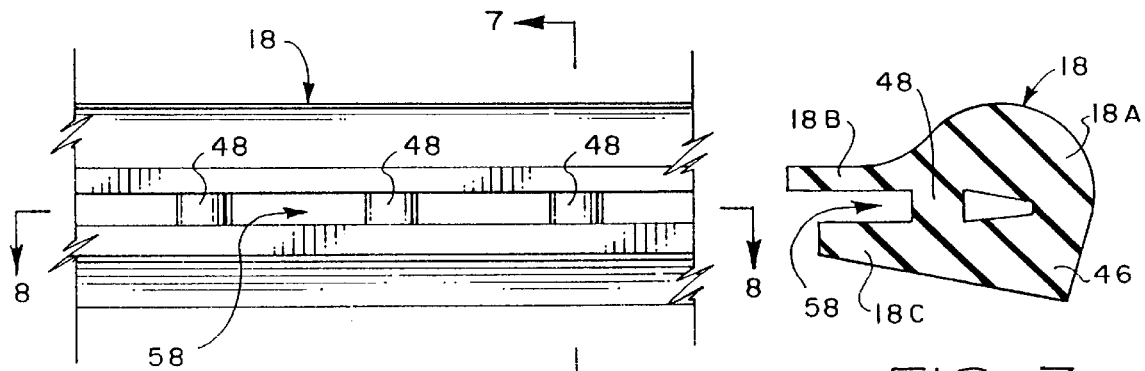
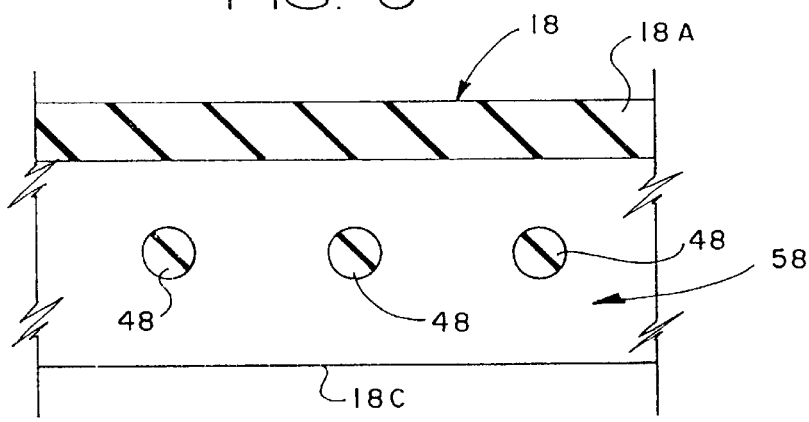
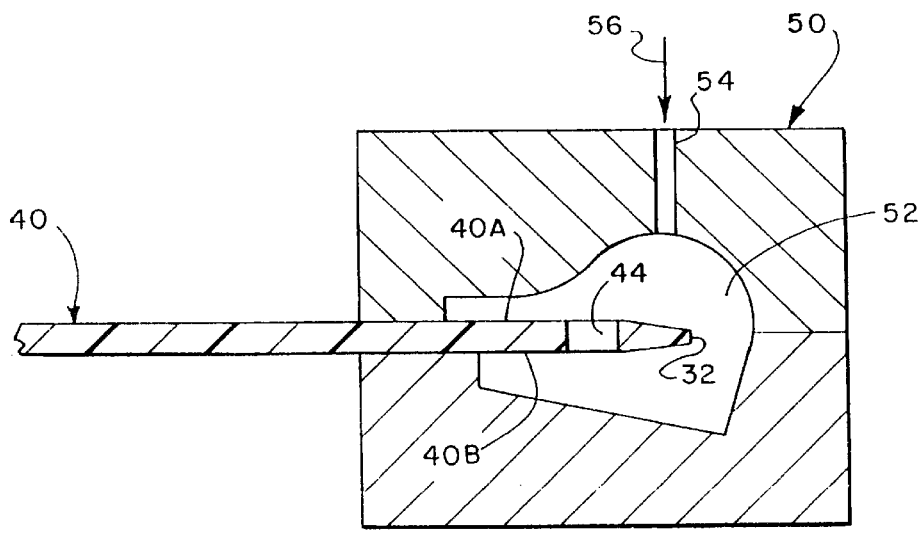

SAFETY GOGGLES HAVING FOAMED-IN-PLACE FACE GASKET

FIELD OF THE INVENTION

This invention relates generally to personal safety equipment and in particular to safety goggles suitable for industrial use.

BACKGROUND OF THE INVENTION

Safety goggles provide limited protection against eye injuries that can be caused by hazardous working conditions. Safety goggles are sometimes worn in combination with a hardhat and include an elastic strap that holds the goggles securely about the wearer's head. Safety goggles shield the wearer's eyes from the impact of projectile materials and from exposure to chemical splash, smoke and other toxic vapors, UV and IR radiation, and heat.

DESCRIPTION OF THE PRIOR ART

Single-aperture, single lens safety goggles are in widespread use. Typically, the goggles include a frame which is molded of a hard durometer but flexible plastic material, and a separately fabricated plastic lens that is either flat or convex in curvature. Generally, safety goggles suitable for industrial use are held securely against the wearer's face by an elastic strap fastened onto opposite sides of the goggles frame.

Preferably, safety goggles should be simple in construction and relatively inexpensive to manufacture, while providing wearing comfort as well as impact and splash protection during extended use under hazardous working conditions. Workers are reluctant to wear safety goggles that are heavy, awkward and uncomfortable, thus making it difficult to comply with industrial safety regulations. Consequently, such safety goggles should be light-weight, easy to put on, conformable to a wide range of facial features, and comfortable to wear.

One conventional safety goggles in widespread use includes a single plastic safety lens that extends across the wearer's field of view and is mounted in a viewing aperture on the forward rim of a flexible, plastic goggles frame, with the rear rim of the goggles frame being contoured or shaped to fit the face of the wearer. The frame and lens thus combine to enclose the space immediately in front and around the wearer's eyes. Safety goggles of this general type are shown in U.S. Pat. No. 3,638,240 assigned to American Allsafe Company, Inc.

Wearing comfort and splash protection have been improved by a soft, compressible face gasket that is attached onto the face engaging rim of the goggles frame. The face gasket, typically made of rubber, provides a non-irritating, cushioning surface that can be worn in skin contact for extended periods with minimum discomfort.

One factor that has limited improvements in face gaskets is the difficulty of attaching the soft, relatively low durometer face gasket material onto the hard, relatively high durometer plastic goggles frame. The face gasket should remain intact and securely attached to the goggles frame while resisting detachment and rupture in response to impact forces and high pressure blow-back conditions as well as during ordinary handling and wear. Another limitation is the difficulty in maintaining a reliable splash seal between the flexible goggles frame and the face gasket, and between the face gasket and the wearer's face.

A preferred material for constructing the goggles frame is synthetic thermoplastic polymer, for example polyvinyl chloride (PVC). Polyvinyl chloride is preferred because it is non-reactive to weathering and moisture, is dimensionally stable, and resists most acids, fats, petroleum hydrocarbons and fungus. Polyvinyl chloride (PVC) is readily compounded into flexible and rigid forms by the use of plasticizers, stabilizers, fillers and other modifiers. Moreover, PVC is available as a foam that can be colored and processed by blow molding and extruding.

The goggles frame should have a relatively hard durometer for impact resistance, and it should also be thin and light-weight for flexibility. The face gasket should be soft and pliable. Consequently, the face gasket can be torn or ruptured by hard fasteners that penetrate through the soft body of the gasket. Although a synthetic polymer such as PVC has good impact resistance, it resists adhesive bonding and can also be torn or ruptured by hard fasteners.

Prior attempts to solve the face gasket attachment problem fall into the following general categories:

1. The face gasket is integrally formed with the goggles frame, thus providing permanent attachment and conforming engagement against the wearer's face. A limitation on this construction is that the synthetic polymer material used for construction of the goggles frame necessarily has a hardness durometer value that is stable under high pressure, high impact conditions, and thus is hard and uncomfortable when placed against the wearer's face. An integrally formed face gasket is disclosed in U.S. Pat. Nos. 4,689,837 and 4,896,380.

2. The face gasket is secured onto the goggles frame by adhesive, for example as shown in U.S. Pat. Nos. 4,665,570 and 5,339,119. As previously described, synthetic polymers such as PVC resist adhesive bonding. Moreover, the adhesives deteriorate in response to long-term exposure to moisture, acids and solar radiation.

3. The face gasket is movably coupled to the goggles frame by a bellows or other intermediate flexible member, either by adhesive or mechanical fasteners, for example as shown in U.S. Pat. No. 4,069,516.

4. The face gasket is attached onto the goggles frame by interlocking mechanical fasteners, for example as shown in U.S. Pat. No. 4,087,865. Interlocking fastener members have not been used successfully in the construction of industrial safety goggles because the interlocking union of relatively soft polymer fasteners can easily be stripped apart in response to high impact, high pressure blow-back forces.

5. The face gasket is captured by an interference fit within a resilient channel or groove formed along the periphery of a resilient frame, for example as shown in U.S. Pat. No. 4,755,040. The interfitting materials must be relatively hard to produce a reliable connection that can withstand high impact forces; because of such hardness, the face gasket cannot provide the wearing comfort needed for long-term, extended wear.

6. The face gasket is attached onto the goggles frame by mechanical fasteners that penetrate the gasket material, for example as shown in U.S. Pat. No. 2,406,608. Penetrating fasteners such as metal screws or stitching are not suitable for high-impact, high-pressure service since either the goggles frame or the gasket can rupture or deform at the penetration points, thus causing detachment or leakage.

For these reasons, there is a continuing interest in improving the wearing comfort as well as the reliability and performance of safety goggles.

SUMMARY OF THE INVENTION

In view of the foregoing limitations on goggles having conventional attachment methods, there is a need for an improved face gasket attachment in which a relatively soft durometer face gasket can be securely attached to a relatively hard durometer goggles frame. The face gasket should be made of a soft, cushioning material that provides long-term wearing comfort, as well as a reliable splash seal and permanent mechanical attachment. The face gasket should seal the interface between the gasket material and the goggles frame, as well as provide a reliable splash seal between the gasket and the wearer's face. The attachment should also be resistant to rupturing, bursting and deformation, and also highly resistant to detachment from the goggles frame.

According to one aspect of the present invention, an improved method is disclosed for attaching and retaining a soft, cushioning face gasket onto an impact-resistant goggles frame that provides long-term wearing comfort while improving the integrity of the splash seal and the mechanical attachment of the face gasket onto the goggles frame. The goggles frame and the face gasket are formed of materials having relatively hard and soft durometer values, respectively, are not integrally formed together, are not secured by adhesive, are not coupled by bellows and are not attached by interlocking edge portions or by hard fasteners that penetrate the face gasket.

The limitations described above are overcome, according to the present invention, by molding the face gasket directly onto the flexible, but relatively hard durometer, impact-resistant goggles frame. The face gasket is molded onto a contoured rim portion of the goggles frame for conformable engagement about the face and forehead of the wearer. The face gasket is made of smooth, low durometer, non-tacky, chemically resistant closed cell polymeric foam material, for example urethane.

The face gasket is permanently attached onto the goggles frame by injecting low viscosity urethane foam into a mold cavity containing the contoured rear marginal rim of the goggles frame so that the contoured rim is embedded within the molded gasket body. Marginal sidewall portions of the goggles frame are intersected by small openings (sprue holes) that permit the pressurized resin foam to flow through the goggles frame sidewall, around the contoured rim of the goggles frame, and along the marginal sidewall surfaces during molding. The contoured marginal rim portion of the goggles frame thus becomes embedded within the molded body portion of the face gasket. Sprue slugs of the resin material fill the sprue openings and thereby define unitary connecting links that permanently secure the face gasket onto the goggles frame.

BRIEF DESCRIPTION OF THE DRAWINGS

Operational features and advantages of the present invention will be understood by those skilled in the art upon reading the detailed description which follows with reference to the attached drawings, wherein:

FIG. 6 is a front elevational view of the face gasket shown in FIG. 2;

FIG. 7 is a right sectional view thereof taken along the lines 7—7 of FIG. 6;

FIG. 8 is a sectional view thereof taken along the line 8—8 of FIG. 6; and,

FIG. 9 is a simplified diagram showing the contoured rim portion of the goggles frame secured within the cavity of a mold.

DETAILED DESCRIPTION OF THE PREFERRED EMBODIMENT

Figure 1:
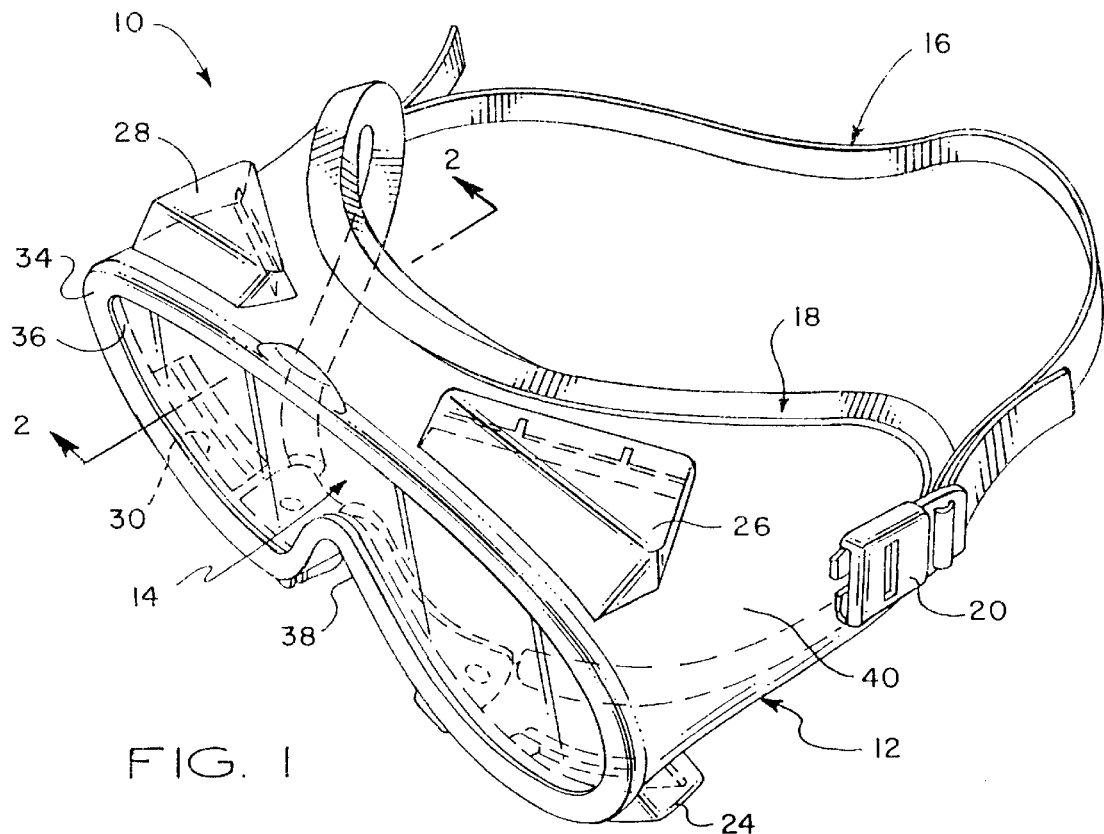
FIG. 1 is a perspective view of safety goggles having a soft, conformable face gasket attached onto a goggles frame according to the foam-in-place method of the present invention.

In the description which follows, like parts are indicated throughout the specification and drawings with the same reference numerals, respectively. The drawing figures are not necessarily to scale and the proportions of certain parts have been exaggerated for sake of clarity.

A safety goggles 10 constructed according to the preferred embodiment of the present invention has four principal components, namely a molded frame 12, an eye protection lens 14, an elastic head strap 16 and a face gasket 18. Opposite ends of the elastic head strap 16 are releasably attached to the goggles frame 12 by bracket fasteners 20, 22, respectively. Shielded ventilation ports 24, 26, 28 and 30 are formed in the goggles frame for permitting indirect circulation of ambient air into the protected space enclosed by the goggles frame 12 while blocking direct entry of chemical splashes.

The goggles frame 12 is preferably constructed of a flexible, impervious, resilient polymer material which is hard enough to provide impact resistance, but is resilient enough to permit its protective sidewall to flex and uniformly conform to the facial contour of the individual wearer. The goggles frame material is preferably a molded thermoplastic polymer material such as flexible polyvinyl chloride (PVC) or acrylic resin.

The eye protection lens 14 is made of a transparent, impact-resistant material such as polycarbonate that will bond with an anti-fogging and/or scratch-resistant coating. The lens 14 may also be treated to reduce the transmission of ultra-violet (UV), infra-red (IR) and laser radiation. Preferably, the eye protection lens 14 is formed in a generally flat, double-ovate orbicular outline.

The goggles frame 12 has a facial contour rim portion 32 that is curved to conform uniformly around the eyes, the forehead and across the nose of the wearer, a forward lens retainer rim 34 which circumscribes a viewing window opening 36, and a flexible bridge 38 which rides on the wearer's nose. The lens retainer rim 34 and the facial contour rim 32 are joined by a continuous, protective sidewall 40 which projects rearwardly and generally in perpendicular relation from the lens retainer rim 34, thereby enclosing the space immediately in front of and surrounding the wearer's eyes.

The eye protection lens 14 has a generally flat, main lens body portion and a peripheral edge portion 14E that is confined within an annular retainer slot 42. The retainer slot 42 is an open, continuous slot that is molded into the lens retainer rim 34.

Figure 2:
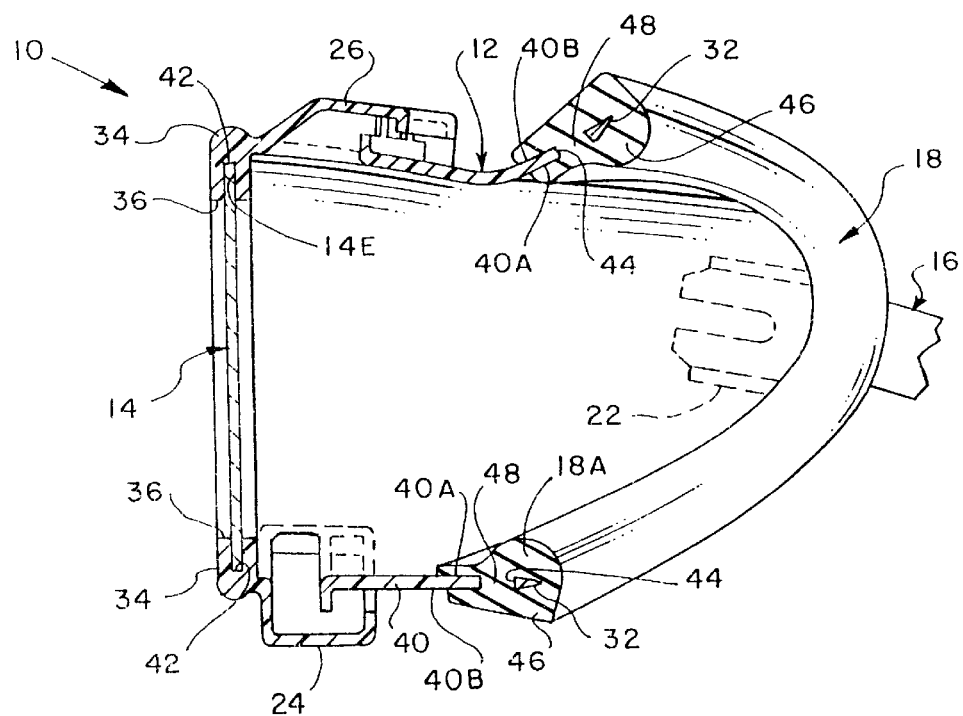
FIG. 2 is a sectional view thereof, taken along the line 2—2 of FIG. 1.
Figure 3:
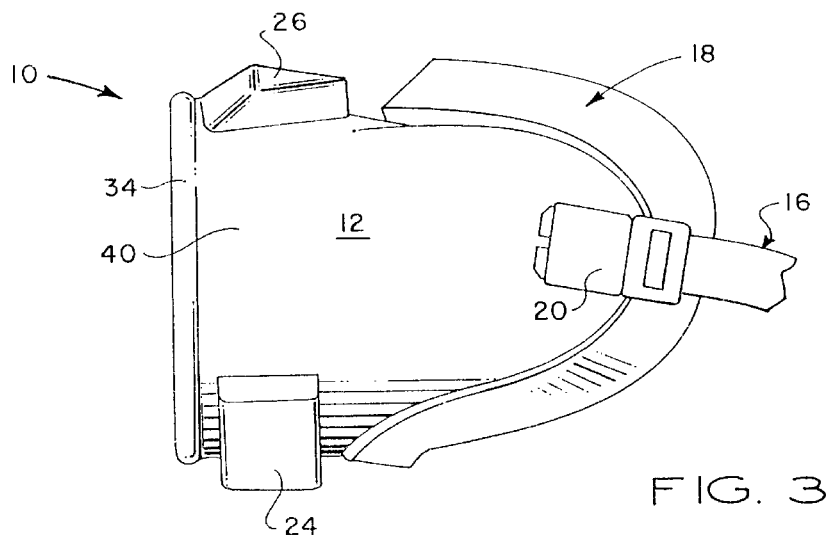
FIG. 3 is a side elevational view thereof.
Figure 4:
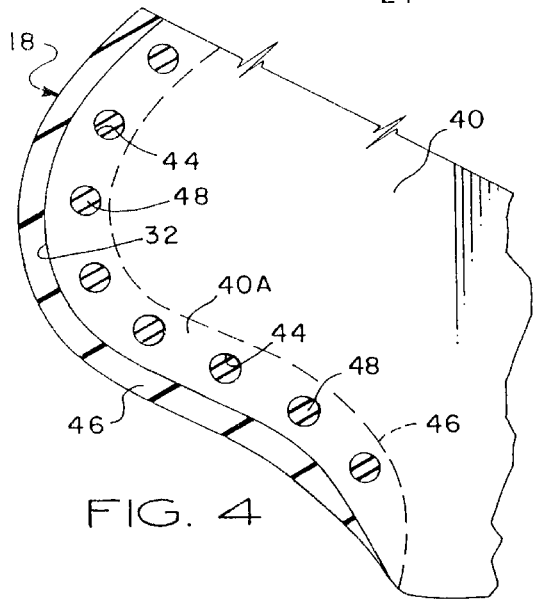
FIG. 4 is a developed plan view, partially in section, of a portion of the goggles frame and foamed-in-place face gasket.
Figure 5:
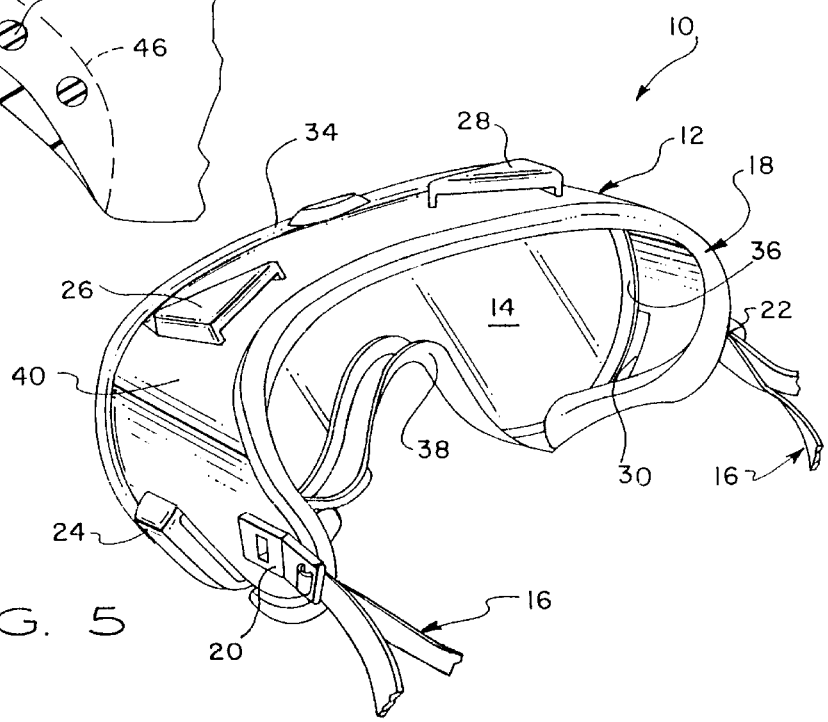
FIG. 5 is a rear perspective view of the safety goggles shown in FIG. 1.

Referring now to FIG. 2, FIG. 3 and FIG. 4, the relatively soft face gasket 18 is attached onto the facial contour rim 32 of the goggles frame for placement in conforming, sealing engagement about the face and forehead of the wearer. According to the present invention, the face gasket 18 consists of a smooth, non-tacky, chemically resistant, washable polymer material. Preferably, the polymer material is a low density, two-component (binary) closed cell foam resin that is pressurized and injected into a mold having a cavity that contains the facial contour rim 32 of the goggles frame 12. One suitable polymer resin is closed cell polyurethane. Another suitable resin is silicone (organo-siloxane) polymer.

According to an important aspect of the present invention, the face gasket 18 is permanently attached onto the goggles frame 12 by molding the face gasket directly onto the protective sidewall 40 so that the contoured rim 32 and the marginal sidewall portions 40A, 40B are embedded within the main body 46 of the soft face gasket 18.

According to a further aspect of the present invention, the protective sidewall 40 and the internal and external side surfaces 40A, 40B are intersected by multiple connecting apertures or sprue holes 44 that are die cut or punched through the sidewall. Preferably, the connecting apertures or sprue holes 44 are circular and have a diameter of about one-eighth inch (about 3 mm). The holes 44 are spaced apart along the contoured peripheral rim 34 and are inset from the contoured rim 32. The small sprue holes 44 permit the pressurized foam resin material to flow through on both side surfaces 40A, 40B of the protective sidewall 40 and around the contoured rim 32 during molding, so that the contoured rim 32 and marginal sidewall surfaces 40A, 40B of the goggles frame 12 are enclosed and embedded within the molded body of soft resin foam material 46.

Other sprue hole sizes and geometries such as oval and rectangular can be used. The number of sprue slugs, the sprue hole geometry, sprue hole spacing and sprue hole size are selected to provide a predetermined frame strength and flexibility, splash resistance, and high resistance to detachment.

The soft face gasket 18 is permanently anchored to the goggles frame by sprue connecting slugs 48 that fill the sprue holes 44. The slugs 48 are integrally formed with the main gasket body 48 and oppose detachment of the gasket 18 from the goggles frame 12. The sprue slugs 48 permanently attach the main body portion 46 of the face gasket material onto the goggles sidewall 40, with the interface between the goggles frame 12 and the face gasket 18 being sealed against leakage.

Referring now to FIG. 6, FIG. 7, FIG. 8 and FIG. 9, the face gasket 18 is molded directly onto the protective goggles sidewall 40 in a mold 50 having an injection cavity 52 and an injection port 54. The contoured rim portion of the goggles sidewall 40 is sealed and secured within the mold cavity 52, with the contoured rim portion being substantially centered within the mold cavity 52. Pressurized resin foam is discharged into the mold cavity 52 through the injection port 54. As the pressurized resin foam fills the mold cavity 52, the pressurized resin foam flows through the sprue openings 44, around the contoured rim 32 and along both sidewall surfaces 40A, 40B until the contoured marginal edge portion of the goggles frame becomes completely embedded within the molded body portion 46 of the face gasket 18. The pressurized resin foam fills the sprue holes 44, thus producing sprue slugs 48 that are integrally formed with the main body portion 46 of the face gasket 18.

As shown in FIG. 6, FIG. 7 and FIG. 8, the molding procedure forms a rounded gasket edge portion 18A, seal flaps 18B, 18C and an elongated open slot 58 which intersects the gasket main body portion 46, thus separating the gasket seal flaps 18B, 18C. As can best be seen in FIG. 7, the sprue slugs 48 span the slot 58, thereby defining integrally formed links connecting the seal flaps 18B, 18C at spaced locations along the length of the face gasket 18.

Referring again to FIG. 2, the sprue slugs 48 (or connecting links) combine with the main body portion 46 to completely encircle the contoured edge portion 32, with the result that the marginal edge portion of the protective sidewall is completely enclosed and embedded within the main body portion 46 of the face gasket 18 and sealed by the gasket seal flaps 18B, 18C.

By this method, the rear contoured edge of the hard durometer goggles frame is sealed within the unitary molded body 46 of soft, low durometer, resilient polymeric foam. The face gasket 18 is permanently anchored to the goggles frame 12 by the sprue slugs 48 that fill the sprue holes 44. The sprue slugs are integrally formed with the main body of the gasket foam material, thus defining unitary connecting links that permanently attach the gasket body in splash resistant sealing engagement around the contoured rim 32 and on both marginal sides 40A, 40B of the goggles frame sidewall.

What is claimed is:

1. A safety goggles comprising an eye protection frame and a face gasket, the eye protection frame including a contoured rim portion embedded within the face gasket, said contoured rim portion including sidewall surfaces that are intersected by multiple connecting apertures which are completely surrounded by said contoured rim portion-and said face gasket including body portions overlapping said sidewall surfaces, and including link portions disposed in the connecting apertures, said link portions being integrally formed with the face gasket body portions.

2. A safety goggles comprising an eye protection frame and a face gasket mounted onto the frame, the eye protection frame having a rim contoured for facial engagement and marginal sidewall surfaces intersected by connecting apertures, the face gasket having a main body portion that is intersected by an open slot and integrally formed connecting links spanning the slot, the marginal sidewall surfaces and contoured rim of the goggles frame being received within the open slot and the integrally formed connecting links extending through the connecting apertures.

3. A safety goggles comprising a unitary molded frame including a lens retainer rim, a lens supported on the retainer rim and a protective sidewall including a curved rim portion disposed adjacent the face of a wearer when the safety goggles is worn in an operative position, and a face gasket attached to the protective sidewall, the face gasket including a main body portion disposed for engagement with a person's face when the safety goggles is worn in the operative position, the curved rim portion being intersected by multiple connecting apertures which are completely surrounded by curved rim portion, the rim portion and connecting apertures being embedded within the main body portion of the face gasket, and the face gasket including attachment link portion integrally formed with the main body portion and extending through the connecting apertures.

4. A safety goggles of the type including a face gasket and an eye protection frame having a contoured rim portion, the contoured rim portion being intersected by a plurality of openings which are completely surrounded by said contoured rim portion and the face gasket is attached onto the contoured rim portion, the face gasket having a main body portion disposed for sealing engagement with a person'which are completely surrounded by said contoured rim portions face and having attachment links integrally formed with the main body portion, the contoured rim portion of the eye protective frame being embedded within the main body portion of the face gasket, and the attachment links extending through the openings.

5. A safety goggles as defined in claim 4, wherein the face gasket comprises a polymer resin, and the face gasket is attached onto the goggles frame by injecting the polymer resin into a mold cavity containing the contoured rim portion until the contoured rim portion is embedded within the resin and the openings are filled with the resin.

6. A safety goggles as defined in claim 5, wherein the polymer resin comprises a closed cell foam.

7. A safety goggles as defined in claim 5, wherein the face gasket comprises a polymer resin selected from the group consisting of polyurethane and silicone (organosiloxane) polymer.

8. A goggles frame as defined in claim 4, wherein the openings are circular apertures having a diameter of approximately one-eighth inch (approximately 3 mm).

9. A method for attaching a face gasket onto the facial contoured rim portion of a goggles frame comprising the steps:

forming a plurality of sprue holes through the contoured rim portion;

securing the contoured rim portion within the cavity of a mold; and, injecting pressurized resin into the mold cavity until the sprue holes are filled by slugs of pressurized resin and the contoured rim portion and sprue holes are embedded within a gasket body formed by the pressurized resin, wherein the slugs are integrally formed with the gasket body.

10. A safety goggles having a contoured rim portion and a face gasket attached onto the contoured rim portion according to the method defined in claim 9, wherein the spur holes are completely surrounded by said contoured rim portion.

* * * * *